(12) United States Patent
Schmidt et al.

(10) Patent No.: US 8,343,948 B2
(45) Date of Patent: Jan. 1, 2013

(54) MEDICAMENT FOR PREVENTING AND/OR TREATING MAMMARY CARCINOMA, CONTAINING A STEROIDAL AROMATASE INHIBITOR

(75) Inventors: Alfred Schmidt, Hamburg (DE); Heinrich Wieland, St. Peter (DE)

(73) Assignee: Curadis GmbH, Enlangen (DE)

(*) Notice: Subject to any disclaimer, the term of this patent is extended or adjusted under 35 U.S.C. 154(b) by 429 days.

(21) Appl. No.: 11/315,003

(22) Filed: Dec. 23, 2005

(65) Prior Publication Data
US 2006/0178353 A1    Aug. 10, 2006

Related U.S. Application Data

(60) Continuation of application No. 10/227,523, filed on Aug. 26, 2002, now abandoned, which is a continuation of application No. 10/016,107, filed on Dec. 17, 2001, now abandoned, which is a division of application No. 09/646,355, filed as application No. PCT/EP99/01374 on Mar. 3, 1999, now abandoned.

(30) Foreign Application Priority Data

Mar. 18, 1998  (EP) .................................. 98104949

(51) Int. Cl.
*A61K 31/56* (2006.01)
(52) U.S. Cl. ....................................................... 514/177
(58) Field of Classification Search .................... 514/177
See application file for complete search history.

(56) References Cited

U.S. PATENT DOCUMENTS 5,945,109 A * 8/1999 Schmidt et al. ............... 424/401

FOREIGN PATENT DOCUMENTS

| EP | 0310542 A1 | 4/1989 |
|----|------------|--------|
| WO | WO-85/03228 | 8/1985 |
| WO | WO-92/10482 | 6/1992 |
| WO | WO-93/25548 | 12/1993 |
| WO | WO-96/08231 | 3/1996 |
| WO | WO-97/36570 | 10/1997 |

OTHER PUBLICATIONS

Brodie et al., Biol. Reprod. 1978, 18(3):365-370.
Brodie et al., Journal of Steroid Biochemistry; 10:423-429, 1979.
Budavari, Merck Index, 11$^{th}$ ed. 1989, p. 513-514, monograph 3247.
Coombes et al., European Journal of Cancer 1992; 28A(12); 1945-1950.
Hanson, "Analgesic, Antipyretic and Anti-inflammatory Drugs" in Remington: The Science and Practice of Pharmacy, 19th ed., 1995, p. 1218.
Remington's Pharmaceutical Sciences, 18$^{th}$ ed., 1990, pp. 1596-1602.
Patent Abstracts, XP-002104191, Dec. 1981.
Patent Abstracts, XP-002104192, Aug. 1982.

* cited by examiner

*Primary Examiner* — Daniel Sullivan
*Assistant Examiner* — Trevor Love
(74) *Attorney, Agent, or Firm* — Milbank, Tweed, Hadley & McCloy LLP

(57) ABSTRACT

A method of prophylaxis and/or treatment of mastocarcinoma (i.e., mammary carcinoma) involves the topical application of a therapeutically or prophylactically effective amount of a steroidal aromatase inhibitor locally, and not systemically, to an area of a patient in need of treatment. This local application avoids the side effects associated with systemic use of steroidal aromatase inhibitors.

12 Claims, 1 Drawing Sheet

MEDICAMENT FOR PREVENTING AND/OR TREATING MAMMARY CARCINOMA, CONTAINING A STEROIDAL AROMATASE INHIBITOR

The invention relates to a medicament for the prophylaxis (primary and secondary prophylaxis) and/or treatment of breast cancer.

Breast cancer is the most frequent malignant disease in women. In Germany, breast cancer makes up about 20% of all cases of cancer in women; the incidence at present is about 30,000 new cases of disease per annum. The adjuvant cancer therapy used today does lead to an increase in the survival rate; breast cancer screening and early surgical treatment can also lower the mortality by over 30%. However, since the number of new cases of disease is continuously increasing, the death raze measured over the total population remains the same or increases. Until now, it has barely been possible to affect the number of new cases, as too little is known about triggering factors.

In approximately half of all breast cancers, oestrogen and/or progesterone receptors are found in the cytoplasm. Breast cancers of this type need oestrogen for the proliferation of their cells. Oestrogens act by binding to specific intracellular (cytoplasmic) receptors of oestrogen-sensitive cells, into which they are passively introduced by diffusion from the plasma. The binding changes the configuration of the receptor protein. The receptor-hormone complex controls both the transcription and the expression of specific genes; the synthesis of growth-promoting and/or growth-inhibiting factors caused thereby finally has an effect on cell growth.

By withdrawal of oestrogens, regression of oestrogen-dependent tumours can be achieved in premenopausal women, the ovaries are the main source of oestrogens. Their surgical removal has therefore been carried out since 1896 with breast cancer in the advanced stage (metastasis formation) as a so-called surgical hormone therapy.

In post-menopausal women, the conversion of adrenal androgens, especially androstenedione and testosterone, to oestrone and oestradiol is the main source of oestrogen. The conversion to oestrogens takes place in the muscle and fatty tissue.

In clinical practice, for over twenty years both early and advanced stages of breast cancer have been treated with tamoxifen or its derivatives (in particular tamoxifen citrate). Tamoxifen occupies the oestrogen receptors located in the cytoplasm of the cancer cells and thus causes competitive displacement of oestrogens. The complex formed from tamoxifen and the oestrogen receptor prevents the transcription and the expression of genes promoting cell growth, which otherwise is caused by a complex formed from oestrogens and the receptor.

In in-vitro experiments, it has been demonstrated that tamoxifen also has a growth-inhibiting and, under certain circumstances, even cytostatic effect on cell lines which have no oestrogen receptors. Tamoxifen inhibits protein kinase C and blocks the activation of calmodulin. It increases the activity of the killer cells and inhibits suppressor T lymphocytes.

In particular after relatively long treatment, tamoxifen can act on cancer cells as well as oestrogens in a manner which is not known in greater detail and promotes their growth. Relatively long-lasting tamoxifen treatment can therefore lead, under certain circumstances, to tumour growth. It moreover leads to a risk which is increased by a factor of 3 to 5 of suffering from cancer of the endometrium. In view of the clinical benefits of tamoxifen therapy, this risk is accepted in breast cancer patients.

The systemic treatment of breast cancers with aromatase inhibitors, in particular 4-hydroxyandrost-4-ene-3,17-dione (INN formestane) is further known. Aromatase is a complex enzyme system which catalyses the conversion of adrenal androgens to oestrone and oestradiol.

Formestane is a derivative of the physiological steroid hormone androstenedione and binds competitively to other substrates of aromatase. During catalysis, it damages the enzyme molecule irreversibly. Systemic treatment with formestane is likewise used as an antioestrogenic breast cancer therapy.

The invention is based on the object of creating a medicament of the type mentioned at the outset, which is suitable for treatment, and in particular also prophylaxis, of breast cancer.

The invention achieves this object by formulating a steroidal aromatase inhibitor to give a medicament intended for topical application. The use of antigestagens as an additional constituent of the medicament is excluded in the context of the invention.

Some terms used in the context of the invention will first be explained.

According to the invention, steroidal aromatase inhibitors are used as substances inhibiting the formation of oestrogens. These inhibit oestrogen biosynthesis from the androgenic precursors, for example the enzymatic conversion of androstenedione to oestrone or of testosterone to oestradiol. Since the two synthesis steps mentioned are mediated by the enzyme system of the aromatase (converting enzyme), aromatase inhibitors are used in the context of the invention. Preferred inhibitors are those which bind to the aromatase and irreversibly damage this. After topical application, they penetrate through the skin and concentrate in the fatty tissue.

The medicament according to the invention is intended for topical application. The medicament is applied locally to the skin, the preferably strongly lipophilic active compound is transdermally absorbed and thus brought locally to the intended site of action. The active compound concentrates in the periductal fatty tissue. In a long-term treatment, the fatty matter of the treated breast is markedly reduced. This reduction decreases the quantity of oestrogen-forming cells having oestrogen-forming competence. The lipophilicity and hydrophobicity of the active compound has the result that the active compound is exclusively concentrated locally in the fatty tissue and can display no systemic action. Oestrogens are understood as meaning all female sex hormones having an action comparable, for example, to that of oestrone and oestradiol.

In the use of aromatase inhibitors known from the prior art, such as formestane, it is intended to transport these to the site of action via the blood circulation. High serum concentrations of the aromatase inhibitor are aimed at, which, in addition to the desired action in the tumour, can lead to systemic side effects. In view of the severity of the illness, such side effects are accepted in acute therapy in view of the success desired. However, this does not come into consideration in the case of a preventive treatment against a still unexisting or clearly detected disease.

According to the invention, however, it is intended to apply the medicament topically immediately on or in the vicinity of the intended site of action. Unlike the prior art, no transport via the blood circulation to the intended site of action is aimed at. According to the invention, the result achieved is an adequate local active compound level in the tissue at risk (in prophylaxis) or in the diseased tissue (in therapy) without a noticeable absorption of the active compound taking place in the blood circulation. The crux of the invention is thus not only in the topical application per se, but in the local topical application in such a way that the active compound concentrates immediately in the tissue at risk and/or diseased tissue, and not indirectly via the blood circulation.

If metastasizing carcinomas are also to be treated and/or prophylaxis is to be carried out against these, the medicament according to the invention can be applied topically to the intended site of action in such an amount that a noticeable absorption in the blood circulation additionally takes place and a serum level thus builds up which also transports the active compound to metastases in this use too, a local absorption on or in the vicinity of the intended site of action also primarily takes place.

The medicament can be used for the treatment of breast cancer. After surgical primary care and, if appropriate, appropriate adjuvant therapy, this treatment can replace and/or supplement the hitherto customary systemic antioestrogenic therapy.

An important advantage of the invention is the possibility of also using the medicament for breast cancer prophylaxis. A particularly advantageous possibility of employment is so-called secondary prophylaxis. In female patients in whom a breast cancer is already present, there is a particularly high risk of a further carcinoma in the contralateral breast. The contralateral breast can then be treated prophylactically with the medicament according to the invention. A secondary prophylactic treatment of the diseased breast to avoid local recurrences is likewise possible.

In the case of so-called high-risk women, primary prophylaxis can be performed. The selection criteria which can be used for such a high-risk group are, for example, the facts that at least one female relative of first degree on the mother's side is or has been suffering from breast cancer on one side before the 45th year of life or bilaterally, or that on the mother's side at least one female relative of first degree and an additional female relative are or have been suffering from breast cancer. Since the local application according to the inventor virtually completely avoids possible systemic side effects of the active compound or account of its hydrophobicity, the indication for primary prophylaxis can be made relatively generously already in the presence of tissue having a comparatively low or average risk (for example histological finding Prechtel II or III). Prophylaxis can be started even if the conventional early diagnosis (palpation finding) is still negative, since this customary early diagnosis is inadequate and as a rule only detects a breast cancer when a systemic disease which is barely still curable is already present.

The medicament according to the invention is preferably applied locally and topically over a relatively long period of time (if needed up to lifelong) and application is carried out, for example, once or twice per day.

The active substances are selected from the group consisting of the (preferably lipid-soluble) steroidal aromatase inhibitors. On topical application, these lipid-soluble substances penetrate into the fatty tissue and locally prevent the de novo formation of oestrogens from the oestrogen precursors.

For example, steroidal aromatase inhibitors such as 4-hydroxyandrost-4-ene-3,17-dione (formestane), 6-methyleneandrostra-1,4-diene-3,17-dione (exemestane), 10-(2-propynyl)estr-4-ene-3,17-dione (MDL 18962) and 7-α-substituted androstenedione derivatives can be used.

The names mentioned in brackets are the INNs (International nonproprietary names). For the terminology and structure of the substances mentioned, reference is likewise made to the "Rote Liste", and Römpp's chemical encyclopaedia.

Until now, the substances mentioned have only been used for the systemic therapy of breast cancer. According to the invention, however, the active compound is brought to the intended site of application by local application. When using aromatase inhibitors, the invention achieves a reduction of the aromatase activity in the fatty tissue of the breast, i.e. exactly in the position in which a tumour can be formed or grow. On relatively long-term use, the fatty matter of the breast and thus the amount of possible risk tissue is reduced. Since breast cancers are frequently formed in upper breast quadrants of increased aromatase activity, particularly effective prophylaxis is possible there according to the invention.

The use according to the invention of aromatase inhibitors can be employed prophylactically or therapeutically even against those tumours of the breast which are themselves able to produce oestrogen or autocrine/paracrine stimulation. A lowering of the oestrogen concentration in the plasma barely has an effect on such tumours, but the reduction of the intratumoral aromatase concentration to be achieved according to the invention can affect such tumours on account of the use of cell-permeable inhibitors.

Since the active compounds administered according to the invention remain localized in the fatty tissue of the breast and display their intended action there on account of their lipid solubility, the side effects induced by systemic application are eliminated. This reduction or exclusion of side effects allows significantly wider prophylactic use. The medicament according to the invention can be applied by patients themselves and frequent visits to the doctor for this purpose are not necessary.

A medicament formulated according to the invention preferably contains formestane.

Formestane derivatives such as, for example, acetylated formestane (for example 4-O-acetylandrost-4-ene-3,17-dione) are likewise preferably utilizable. The acetylation of the formestane increases its hydrophilicity and thus skin penetration significantly. Since the acetyl group is hydrolysed under the conditions prevailing in the subcutaneous region after passage through the skin, the actual active compound formestane is formed again in situ. When using such an acetylated formestane, a precursor of the actual active compound penetrating better through the skin is thus applied and the inventors have recognized that the actual active compound is formed in situ subcutaneously from this precursor.

As a rule, the active compounds used according to the invention are lipid-soluble and highly suitable for topical application. As already described above, the concentration in the fatty tissue of the breast avoids systemic side effects. To improve the skin penetration, substances known in the prior art which promote this can be added to the medicament according to the invention, for example hyaluronidases or DMSO (dimethyl sulphoxide).

The medicament Is preferably formulated as an ointment, cream, gel, emulsion or lotion. Formulation as a powder or oil is also conceivable. Formulation bases are familiar to the person skilled in the art from the cosmetic and pharmaceutical industry and do nor need to be explained here in greater detail. For example, vegetable oils and fats such as almond oil, peanut oil, olive oil, peach kernel oil, castor oil, plant extracts, ethereal oils; furthermore vegetable waxes and synthetic and animal oils, fats or waxes; lecithin, lanolin alcohols, carotene, fragrances, mono- or polyhydric alcohols, urea, preservatives and colourants etc. can be used. Formulation as an oil-in-water or water-in-oil emulsion is preferred.

The active compound content of she medicament (the content of substances inhibiting the formation of oestrogens) can be between 0.0001 and 20% by weight, preferably 0.6 and 10% by weight, further preferably 1 and 5% by weight. A customary range is 0.6 to 2% by weight.

If substances are admixed to promote skin penetration absorption, their content, when using hyaluronidases, can be, for example, between 0.01 and 1% by weight, preferably 0.05 and 0.2% by weight; when using DMSO between 1 and 25% by weight, preferably 5 and 10% by weight.

Embodiments of the invention are described below. In the drawing.

EXAMPLE 1

The following constituents were mixed to give a cream:

| | |
|---|---|
| Urea | 10 g |
| Titanium oxide | 15 g |
| Crude petroleum jelly | 20 g |
| Isopropyl palmitate | 10 g |
| Hardened peanut oil | 10 g |
| Tween 80 | 5 g |
| Formestane | 1 g |
| made up with purified water to | 100 g |

EXAMPLE 2

A gel was prepared from the following constituents:

| | |
|---|---|
| Ethanol 90% | 7.0 g |
| Carbopol$^R$ 934 P | 7.0 g |
| Triethanolamine | 2 g |
| Polysorbate 80 | 5.0 g |
| Glycerol | 3.0 g |
| Formestane | 0.75 g |
| purified water to | 100 g |

EXAMPLE 3

A cream was prepared from the following constituents:

| | |
|---|---|
| Propylene glycol | 25.0 g |
| Isopropyl myristate | 6.0 g |
| Sorbitan monostearate | 1.0 g |
| Polysorbate 80 | 2.0 g |
| Cetylstearyl alcohol | 6.0 g |
| Stearyl alcohol | 2.0 g |
| Glycerol monostearate | 1.0 g |
| Hyaluronic acid | 0.1 g |
| Formestane | 1.5 g |
| purified water to | 100 g |

EXAMPLE 4

A cream was prepared from the following constituents. The constituents are indicated in this example by their INCI names.

| INCI | |
|---|---|
| Ceteareth-25 | 3.0 g |
| PEG-4-polyglyceryl 2-stearate | 2.0 g |
| Cetearyl alcohol | 4.9 g |
| Petrolatum | 10.0 g |
| Paraffinum perliquidum | 3.0 g |
| Sodium carbomer 400 | 0.14 g |
| Lactic acid | 0.02 g |
| Paraffinum perliquidum | 2.0 g |
| Phenoxyethanol, dehydroacetic acid, benzoic acid | 0.4 g |
| Perfume | 0.08 g |
| Formestane | 1.5 g |
| made up with water to | 100 g |

The mixture of phenoxyethanol, dehydroacetic acid and benzoic acid mentioned in the formulation is obtainable from Schülke & Mayr under the name Euxyl$^R$ K702.

EXAMPLE 5

A cream was prepared from the following constituents, which are indicated by their INCI names.

| INCI | |
|---|---|
| Ceteareth-25 | 3.0 g |
| PEG-4-polyglyceryl 2-stearate | 2.0 g |
| Cetearyl alcohol | 4.9 g |
| Petrolatum | 10.0 g |
| Paraffinum perliquidum | 3.0 g |
| Sodium carbomer 400 | 0.14 g |
| Lactic acid | 0.02 g |
| Paraffinum perliquidum | 2.0 g |
| Phenoxyethanol, dehydroacetic acid, benzoic acid | 0.4 g |
| Perfume | 0.08 g |
| 4-acetylandrost-4-ene-3,17-dione (acetylated formestane) | 1.5 g |
| made up with water to | 100 g |

EXAMPLE 6

A clinical zest of the recipe according to Example 1 was carried out. The findings of oversize breasts and medium-grade mastopathy were present in the 25-year-old volunteer.

Figure 1:
FIG. 1 shows the cytological result of a fatty cell aspirate before use of the medicament according to the invention.

A fine needle aspirate of the fatty tissue (0.6 mm puncture needle, fixation in absolute ethanol, staining: May-Grünwald-Giemsa) was withdrawn (FIG. 1). Distended fat cells and eccentric cell nuclei as a result of a high oestrogen influx are detected.

Figure 2:
FIG. 2 shows the corresponding result after daily use over the course of 3 months.

The volunteer then applied the cream according to Example 1 twice daily over a period of 3 months. FIG. 2 shows the fatty tissue aspirate after this use. A reduction in volume of the fatty tissue ("shrivelled" fat cells in a regular arrangement) and an increase in connective tissue is detected due to the aromatase inhibition. The results showed a reduction of the tissue at risk by about 50% and a distinct firming of connective tissue and skin.

The invention claimed is:
1. A method for treating breast cancer comprising:
identifying a subject in need thereof;
administering topically a therapeutically effective dose of a medicament to said subject, wherein said medicament comprises a steroidal aromatase inhibitor other than an antigestagen, to thereby treat breast cancer, wherein said medicament comprises a steroidal aromatase inhibitor content of 0.0001 to 20% by weight.

2. The method of claim 1 wherein said steroidal aromatase inhibitor comprises formestane (4-hydroxyandrost-4-ene-3,17-dione) and a pharmacologically active formestane derivative.

3. The method of claim 1 wherein said steroidal aromatase inhibitor comprises formestane (4-hydroxyandrost-4-ene-3,17-dione) or a pharmacologically active formestane derivative.

4. The method of claim 2 or 3 wherein said formestane derivative comprises acetylated formestane.

5. The method of claim 1 wherein said medicament further comprises substances for promoting skin penetration.

6. The method of claim 1 wherein said medicament further comprises DMSO.

7. The method of claim 1 wherein said medicament is formulated as an ointment, cream, gel, emulsion or lotion.

8. The method of claim 1 wherein said medicament comprises an active compound content of 0.6 to 10% by weight.

9. The method of claim 1 wherein said medicament comprises an active compound content of 1 to 5% by weight.

10. The method of claim 1 wherein said medicament comprises an active compound content of 0.6 to 2% by weight.

11. The method of claim 1 wherein said steroidal aromatase inhibitor comprises formestane (4-hydroxyandrost-4-ene-3,17-dione).

12. The method of claim 4 wherein said acetylated formestane derivative comprises 4-O-acetylandrost-4-ene-3,17-dione.

* * * * *